United States Patent
Black

(10) Patent No.: US 6,284,515 B1
(45) Date of Patent: Sep. 4, 2001

(54) SIGNAL RECOGNITION PARTICLE POLYPEPTIDES AND POLYNUCLEOTIDES

(75) Inventor: Michael T. Black, Chester Springs, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/035,382

(22) Filed: Mar. 5, 1998

Related U.S. Application Data

(60) Provisional application No. 60/057,890, filed on Sep. 3, 1997.

(51) Int. Cl.$^7$ .................................................. C12N 15/00
(52) U.S. Cl. ........................ 435/252.3; 435/6; 435/320.1; 536/23.1; 536/23.7
(58) Field of Search ............................... 536/23.7; 435/6, 435/320.1, 252.3–252.33; 530/350

(56) References Cited

FOREIGN PATENT DOCUMENTS

0786519 * 7/1997 (EP).
0902087A 3/1999 (EP).

OTHER PUBLICATIONS

Critical Synergy: The Biotechnology Industry and Intellectual Property Protection, Biotechnology Industry Organization, Washington, D.C., 1994, pp. 75 and 100–107.*

Desnottes, J.–F; "New targets and strategies for the development of antibacterial agents." *Trends in Biotechnology*, vol. 14, No. 4, pp. 134–140.

Honda, et al: "Cloning and Characterization of a Bacillus Subtilis Gene Encoding a Homolog of the 54–Kilodalton Subunit of Mammalian Signal Recognition Particle and *Escherichia coli* FFH" *Journal of Bacteriology*, vol. 175, No. 15, pp. 4885–4894.

Shibata, et al: "Depletion of Small Cytoplasmic RNA Confers Fusidic–Acid Resistance on Bacillus Subtilis" *Biochemical and Biophysical Research Communication* vol. 210, No. 2, May 16, 1995, pp. 317–323.

Bystroem, et al: "Signal Recognition Particle Protein" *Swissprot Database*, Accession No. P07019, Apr. 1, 1988.

Luirink, et al: "Signal–sequence Recognition by an *Escherichia coli* Ribonucleoprotein Complex" *Nature*, vol. 359, pp. 741–743, Oct. 22, 1992.

EP search report from corresponding European patent application NO. EP98306742.2.

* cited by examiner

*Primary Examiner*—James Martinell
(74) *Attorney, Agent, or Firm*—Edward R. Gimmi; Thomas S. Deibert; William T. King

(57) ABSTRACT

This invention relates to a novel bacterial ribonucleoprotein complex and the component parts thereof. More specifically, this invention relates to SRP isolated from *Staphylococcus aureus* and the use of SRP or components thereof in screens for the identification of antimicrobial compounds and to the use of such compounds in therapy.

10 Claims, No Drawings

SEQUENCE LISTING

<160> NUMBER OF SEQ ID NOS: 8

<210> SEQ ID NO 1
<211> LENGTH: 1368
<212> TYPE: DNA
<213> ORGANISM: Staphylococcus aureus

<400> SEQUENCE: 1

```
atggcatttg aaggcttatc agaacgcctg caagcgacga tgcaaaaaat gcgtggtaag      60
ggtaaactta ctgaagctga tataaagata atgatgcgtg aagtaagatt agcgttattt     120
gaggctgacg taaactttaa agtggtaaaa gaatttatta aaacagtatc agaacgcgca     180
ttaggttccg atgtaatgca atcattaaca ccagggcaac aagttattaa atagttcaa     240
gatgaattaa cgaagttgat gggtggagaa aatacatcga ttaatatgtc aaataaacca     300
cctactgttg ttatgatggt tggtttacaa ggtgctggta aacaacaac tgcaggtaaa     360
ttagcattat tgatgcgtaa aaaatacaac aaaaaaccta tgttagttgc agcagatatt     420
tatcgtccag cagcgataaa tcaattacaa acagtaggga acaaattga tattcctgta     480
tacagtgaag gagatcaagt aaagccacaa caaattgtaa ctaatgcatt aaaacatgct     540
aaagaagaac atttagactt tgtaatcatt gatacagcag gtcgattaca catcgatgaa     600
gcattgatga acgaattaaa agaagtaaaa gaattgcta aaccaaacga aattatgtta     660
gttgtcgatt caatgacggg tcaagatgct gtcaatgttg cagaatcttt tgacgatcaa     720
cttgatgtca caggtgttac cttaactaaa ttagatggtg atacacgtgg tggtgcagct     780
ttatctattc gttcggtgac acaaaaacca attaaattg ttggtatgag tgaaaagtta     840
gatggtttag agctattcca tcctgaacgt atggcatcac gtattttagg tatgggtgat     900
gtgttaagtt taattgaaaa agcgcaacaa gatgtggatc aagaaaaagc aaaagattta     960
gagaaaaaga tgcgtgagtc atcgtttact ttagatgatt ttttagaaca acttgatcag    1020
gtgaaaaatc taggaccact ggatgatatt atgaaaatga ttccaggtat gaataaaatg    1080
aaagggctag ataagcttaa tatgagtgaa aagcaaattg atcatattaa agcgattatc    1140
cagtcaatga cgccggctga agaaacaat ccagacacat tgaatgtatc acgtaaaaag    1200
cgtattgcta aagggtctgg tcgttcatta caagaagtca atcgtttgat gaaacaattt    1260
aacgatatga gaaaatgat gaaacaattc actggtggcg gtaaaggtaa aaaaggtaaa    1320
cgcaatcaaa tgcaaaatat gttaaaaggt atgaatttac cgttttaa                1368
```

<210> SEQ ID NO 2
<211> LENGTH: 455
<212> TYPE: PRT
<213> ORGANISM: Staphylococcus aureus

<400> SEQUENCE: 2

```
Met Ala Phe Glu Gly Leu Ser Glu Arg Leu Gln Ala Thr Met Gln Lys
  1               5                  10                  15

Met Arg Gly Lys Gly Lys Leu Thr Glu Ala Asp Ile Lys Ile Met Met
                 20                  25                  30

Arg Glu Val Arg Leu Ala Leu Phe Glu Ala Asp Val Asn Phe Lys Val
             35                  40                  45

Val Lys Glu Phe Ile Lys Thr Val Ser Glu Arg Ala Leu Gly Ser Asp
         50                  55                  60

Val Met Gln Ser Leu Thr Pro Gly Gln Gln Val Ile Lys Ile Val Gln
```

```
                          -continued
65                  70                  75                  80

Asp Glu Leu Thr Lys Leu Met Gly Gly Glu Asn Thr Ser Ile Asn Met
                85                  90                  95

Ser Asn Lys Pro Pro Thr Val Val Met Val Gly Leu Gln Gly Ala
            100                 105                 110

Gly Lys Thr Thr Thr Ala Gly Lys Leu Ala Leu Leu Met Arg Lys Lys
            115                 120                 125

Tyr Asn Lys Lys Pro Met Leu Val Ala Ala Asp Ile Tyr Arg Pro Ala
130                 135                 140

Ala Ile Asn Gln Leu Gln Thr Val Gly Lys Gln Ile Asp Ile Pro Val
145                 150                 155                 160

Tyr Ser Glu Gly Asp Gln Val Lys Pro Gln Gln Ile Val Thr Asn Ala
                165                 170                 175

Leu Lys His Ala Lys Glu His Leu Asp Phe Val Ile Ile Asp Thr
                180                 185                 190

Ala Gly Arg Leu His Ile Asp Glu Ala Leu Met Asn Glu Leu Lys Glu
            195                 200                 205

Val Lys Glu Ile Ala Lys Pro Asn Glu Ile Met Leu Val Val Asp Ser
210                 215                 220

Met Thr Gly Gln Asp Ala Val Asn Val Ala Glu Ser Phe Asp Asp Gln
225                 230                 235                 240

Leu Asp Val Thr Gly Val Thr Leu Thr Lys Leu Asp Gly Asp Thr Arg
                245                 250                 255

Gly Gly Ala Ala Leu Ser Ile Arg Ser Val Thr Gln Lys Pro Ile Lys
            260                 265                 270

Phe Val Gly Met Ser Glu Lys Leu Asp Gly Leu Glu Leu Phe His Pro
            275                 280                 285

Glu Arg Met Ala Ser Arg Ile Leu Gly Met Gly Asp Val Leu Ser Leu
290                 295                 300

Ile Glu Lys Ala Gln Gln Asp Val Asp Gln Glu Lys Ala Lys Asp Leu
305                 310                 315                 320

Glu Lys Lys Met Arg Glu Ser Ser Phe Thr Leu Asp Asp Phe Leu Glu
                325                 330                 335

Gln Leu Asp Gln Val Lys Asn Leu Gly Pro Leu Asp Asp Ile Met Lys
            340                 345                 350

Met Ile Pro Gly Met Asn Lys Met Lys Gly Leu Asp Lys Leu Asn Met
            355                 360                 365

Ser Glu Lys Gln Ile Asp His Ile Lys Ala Ile Ile Gln Ser Met Thr
370                 375                 380

Pro Ala Glu Arg Asn Asn Pro Asp Thr Leu Asn Val Ser Arg Lys Lys
385                 390                 395                 400

Arg Ile Ala Lys Gly Ser Gly Arg Ser Leu Gln Glu Val Asn Arg Leu
                405                 410                 415

Met Lys Gln Phe Asn Asp Met Lys Lys Met Met Lys Gln Phe Thr Gly
            420                 425                 430

Gly Gly Lys Gly Lys Lys Gly Lys Arg Asn Gln Met Gln Asn Met Leu
            435                 440                 445

Lys Gly Met Asn Leu Pro Phe
450                 455

<210> SEQ ID NO 3
<211> LENGTH: 792
<212> TYPE: DNA
<213> ORGANISM: Staphylococcus aureus
```

<400> SEQUENCE: 3

```
atggcatttg aaggcttatc agaacgcctg caagcgacga tgcaaaaaat gcgtggtaag      60
ggtaaactta ctgaagctga tataaagata atgatgcgtg aagtaagatt agcgttattt     120
gaggctgacg taaactttaa agtggtaaaa gaatttatta aaacagtatc agaacgcgca     180
ttaggttccg atgtaatgca atcattaaca ccagggcaac aagttattaa aatagttcaa     240
gatgaattaa cgaagttgat gggtggagaa atacatcga ttaatatgtc aaataaacca     300
cctactgttg ttatgatggt tggtttacaa ggtgctggta aacaacaac tgcaggtaaa     360
ttagcattat tgatgcgtaa aaaatacaac aaaaaaccta tgttagttgc agcagatatt     420
tatcgtccag cagcgataaa tcaattacaa acagtaggga acaaattga tattcctgta     480
tacagtgaag gagatcaagt aaagccacaa caaattgtaa ctaatgcatt aaaacatgct     540
aaagaagaac atttagactt tgtaatcatt gatacagcag gtcgattaca catcgatgaa     600
gcattgatga acgaattaaa agaagtaaaa gaaattgcta aaccaaacga aattatgtta     660
gttgtcgatt caatgacggg tcaagatgct gtcaatgttg cagaatcttt tgacgatcaa     720
cttgatgtca caggtgttac cttaactaaa ttagatggtg atacccgtgg tggtgcagct     780
ttatctattc gt                                                         792
```

<210> SEQ ID NO 4
<211> LENGTH: 264
<212> TYPE: PRT
<213> ORGANISM: Staphylococcus aureus

<400> SEQUENCE: 4

```
Met Ala Phe Glu Gly Leu Ser Glu Arg Leu Gln Ala Thr Met Gln Lys
  1               5                  10                  15

Met Arg Gly Lys Gly Lys Leu Thr Glu Ala Asp Ile Lys Ile Met Met
             20                  25                  30

Arg Glu Val Arg Leu Ala Leu Phe Glu Ala Asp Val Asn Phe Lys Val
         35                  40                  45

Val Lys Glu Phe Ile Lys Thr Val Ser Glu Arg Ala Leu Gly Ser Asp
     50                  55                  60

Val Met Gln Ser Leu Thr Pro Gly Gln Val Ile Lys Ile Val Gln
 65                  70                  75                  80

Asp Glu Leu Thr Lys Leu Met Gly Gly Glu Asn Thr Ser Ile Asn Met
                 85                  90                  95

Ser Asn Lys Pro Pro Thr Val Val Met Met Val Gly Leu Gln Gly Ala
            100                 105                 110

Gly Lys Thr Thr Thr Ala Gly Lys Leu Ala Leu Leu Met Arg Lys Lys
        115                 120                 125

Tyr Asn Lys Pro Met Leu Val Ala Ala Asp Ile Tyr Arg Pro Ala
    130                 135                 140

Ala Ile Asn Gln Leu Gln Thr Val Gly Lys Gln Ile Asp Ile Pro Val
145                 150                 155                 160

Tyr Ser Glu Gly Asp Gln Val Lys Pro Gln Gln Ile Val Thr Asn Ala
                165                 170                 175

Leu Lys His Ala Lys Glu His Leu Asp Phe Val Ile Ile Asp Thr
            180                 185                 190

Ala Gly Arg Leu His Ile Asp Glu Ala Leu Met Asn Glu Leu Lys Glu
        195                 200                 205

Val Lys Glu Ile Ala Lys Pro Asn Glu Ile Met Leu Val Val Asp Ser
```

```
           210              215              220
Met Thr Gly Gln Asp Ala Val Asn Val Ala Glu Ser Phe Asp Asp Gln
225              230              235              240

Leu Asp Val Thr Gly Val Thr Leu Thr Lys Leu Asp Gly Asp Thr Arg
             245              250              255

Gly Gly Ala Ala Leu Ser Ile Arg
         260

<210> SEQ ID NO 5
<211> LENGTH: 500
<212> TYPE: DNA
<213> ORGANISM: Staphylococcus aureus

<400> SEQUENCE: 5
aaacatcttg caaatgaatt taaatttaac gacttctcaa gacgtcgtat aaagtaaaca      60
atgatataaa tgatttatac ttgcaattaa ctattaaaat atagtaatat atatcttgcc     120
gtgctaggtg gggaggtagc ggttccctgt actcgaaatc cgctttatgc gaggcttaat     180
tcctttgttg aggccgtatt tttgcgaagt ctgcccaaag cacgtagtgt ttgaagattt     240
cggtcctatg caatatgaac ccatgaacca tgtcaggtcc tgacggaagc agcattaagt     300
ggatcatcat atgtgccgta gggtagccga gatttagcta acgactttgg ttacgttcgt     360
gaattacgtt cgatgcttag gtgcacggtt tttattttt taaatattaa accgattatt      420
aagagttgaa aatatatatt tatttataga agctactttc ttgaagacaa ttcagcgtat     480
tatacgtgga acatgtttgt                                                500

<210> SEQ ID NO 6
<211> LENGTH: 358
<212> TYPE: DNA
<213> ORGANISM: Staphylococcus aureus

<400> SEQUENCE: 6
acttgcaatt aactattaaa atatagtaat atatatcttg ccgtgctagg tggggaggta      60
gcggttccct gtactcgaaa tccgctttat gcgaggctta attcctttgt tgaggccgta    120 ttttgcgaa gtctgcccaa agcacgtagt gtttgaagat ttcggtccta tgcaatatga    180
acccatgaac catgtcaggt cctgacggaa gcagcattaa gtggatcatc atatgtgccg    240
tagggtagcc gagatttagc taacgacttt ggttacgttc gtgaattacg ttcgatgctt    300
aggtgcacgg ttttttattt tttaaatatt aaaccgatta ttaagagttg aaaatata      358

<210> SEQ ID NO 7
<211> LENGTH: 276
<212> TYPE: DNA
<213> ORGANISM: Staphylococcus aureus

<400> SEQUENCE: 7
cttgccgtgc taggtgggga ggtagcggtt ccctgtactc gaaatccgct ttatgcgagg      60
cttaattcct tgttgaggc cgtattttg cgaagtctgc ccaaagcacg tagtgtttga    120
agatttcggt cctatgcaat atgaacccat gaaccatgtc aggtcctgac ggaagcagca    180
ttaagtggat catcatatgt gccgtagggt agccgagatt tagctaacga ctttggttac    240
gttcgtgaat tacgttcgat gcttaggtgc acggtt                              276

<210> SEQ ID NO 8
<211> LENGTH: 275
<212> TYPE: DNA
```

```
<213> ORGANISM: Staphylococcus aureus
<220> FEATURE:
<221> NAME/KEY: misc_feature
<222> LOCATION: (1)...(275)
<223> OTHER INFORMATION: n = A,T,C or G

<400> SEQUENCE: 8
aacaatgccg tttcaatata atatttcaaa acatcttgca aatgaattta aatttaccga        60
cttctcaaga cgtcgtataa agtaaacaat gatataaatg atttatactt gcaattaact       120
attnaaatat agtaatatat atctttccgt gctaggtggg gaggtagcgg ttccctgtac       180
tcgaaatccg ctttatgcga ggcttaattc ctttgttgag gccgtattt tgcgaagtct       240 gcccaaagca cgtagtgttt gaagatttcg gtcct                                  275
```

SIGNAL RECOGNITION PARTICLE POLYPEPTIDES AND POLYNUCLEOTIDES

This application claims benefit of provisional application 60/057890, filed Sep. 3, 1997.

FIELD OF THE INVENTION

This invention relates to newly identified polynucleotides, polypeptides encoded by certain of these polynucleotides, molecular complexes of RNAs and polypeptides, the uses of such polynucleotides and polypeptides, as well as the production of such polynucleotides and polypeptides and recombinant host cells transformed with the polynucleotides. The invention relates particularly to such polynucleotides and polypeptides from Staphylococci, especially *S. aureus*. This invention also relates to inhibiting the biosynthesis, assembly or action of such polynucleotides and/or polypeptides and to the use of such inhibitors in therapy.

BACKGROUND OF THE INVENTION

This invention relates to a novel bacterial ribonucleoprotein complex and the component parts thereof. More specifically, this invention relates to SRP, particularly SRP from *Staphylococcus aureus*, and the use of SRP or components thereof in screens for the identification of antimicrobial compounds and to the use of such compounds in therapy.

The Staphylococci make up a medically important genera of microbes. They are known to produce two types of disease, invasive and toxigenic. Invasive infections are characterized generally by abscess formation effecting both skin surfaces and deep tissues. *S. aureus* is the second leading cause of bacteremia in cancer patients. Osteomyelitis, septic arthritis, septic thrombophlebitis and acute bacterial endocarditis are also relatively common. There are at least three clinical conditions resulting from the toxigenic properties of Staphylococci. The manifestation of these diseases result from the actions of exotoxins as opposed to tissue invasion and bacteremia. These conditions include: Staphylococcal food poisoning, scalded skin syndrome and toxic shock syndrome.

The frequency of *Staphylococcus aureus* infections has risen dramatically in the past 20 years. This has been attributed to the emergence of multiply antibiotic resistant strains and an increasing population of people with weakened immune systems. It is no longer uncommon to isolate *Staphylococcus aureus* strains which are resistant to some or all of the standard antibiotics. This has created a demand for both new anti-microbial agents and diagnostic tests for this organism.

While certain Staphylococcal proteins associated with pathogenicity have been identified, e.g., coagulase, hemolysins, leucocidins and exo- and enterotoxins, additional targets are always useful because it is appreciated that the target of a antimicrobial screen can often bias the outcome. Thus, new targets allow for the discovery of new classes of antimicrobials.

BRIEF DESCRIPTION OF THE INVENTION

This invention provides a novel ribonucleoprotein complex, particularly such complex from *Staphylococcus aureus*, and the separately isolated RNA and protein components thereof.

In accordance with another aspect of the present invention, there are provided polynucleotides (DNA or RNA) which encode the protein and RNA components of such a complex.

In particular the invention provides polynucleotides having the DNA sequences given herein.

The invention also relates to novel oligonucleotides derived from the sequences given herein which can act, for example, as antisense inhibitors of the expression of the RNA or protein components. The oligonucleotides or fragments or derivatives thereof can be used to directly inhibit binding or other biological activity or indirectly inhibit activity by interference with RNA protein complex formation. The protein and the RNA components, either separately or in a complex, are also useful as targets in screens designed to identify antimicrobial compounds.

It is an object of the invention to provide polypeptides that have been identified as novel SRP polypeptides by homology between known amino acid sequences, such as *B. subtilis* Ffh and *E. coli* Ffh.

It is a further object of the invention to provide polynucleotides that encode SRP polypeptides, particularly polynucleotides that encode the polypeptide herein designated Ffh, as well as polynucleotides that are transcribed into SRP RNA, particularly polynucleotides that encode the RNA herein designated Ffs.

In a particularly preferred embodiment of the invention the polynucleotide comprises a region encoding Ffh polypeptides comprising the sequence set out in Table 1 [SEQ ID NO:1] which includes a full length gene, or a variant thereof.

In another particularly preferred embodiment of the invention there is a novel Ffh protein from *Staphylococcus aureus* comprising the amino acid sequence of Table 1 [SEQ ID NO:2], or a variant thereof.

In accordance with another aspect of the invention there is provided an isolated nucleic acid molecule encoding a mature polypeptide expressible by the *Staphylococcus aureus* WCUH 29 strain contained in the deposited strain.

A further aspect of the invention there are provided isolated nucleic acid molecules encoding SRP, particularly *Staphylococcus aureus* SRP, including mRNAs, cDNAs, genomic DNAs and structural RNAs. Further embodiments of the invention include biologically, diagnostically, prophylactically, clinically or therapeutically useful variants thereof, and compositions comprising the same.

In accordance with another aspect of the invention, there is provided the use of a polynucleotide of the invention for therapeutic or prophylactic purposes, in particular genetic immunization. Among the particularly preferred embodiments of the invention are naturally occurring allelic variants of SRP and polypeptides encoded thereby.

Another aspect of the invention there are provided novel polypeptides of *Staphylococcus aureus* referred to herein as Ffh as well as biologically, diagnostically, prophylactically, clinically or therapeutically useful variants thereof, and compositions comprising the same.

Among the particularly preferred embodiments of the invention are variants of Ffh polypeptide encoded by naturally occurring alleles of the ffh gene.

In a preferred embodiment of the invention there are provided methods for producing the aforementioned Ffh polypeptides.

In accordance with yet another aspect of the invention, there are provided inhibitors to such polypeptides, useful as antibacterial agents, including, for example, antibodies.

In accordance with certain preferred embodiments of the invention, there are provided products, compositions and methods for assessing SRP expression, treating disease, for example, disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhoea, splenic abscess, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric absces, toxic shock syndrome), skin (e.g., impetigo, folliculitis, cutaneous abscesses, cellulitis, wound infection, bacterial myositis) bone and joint (e.g., septic arthritis, osteomyelitis), assaying genetic variation, and administering a Ffh polypeptide or polynucleotide to an organism to raise an immunological response against a bacteria, especially a *Staphylococcus aureus* bacteria.

In accordance with certain preferred embodiments of this and other aspects of the invention there are provided polynucleotides that hybridize to SRP polynucleotide sequences, particularly under stringent conditions.

In certain preferred embodiments of the invention there are provided antibodies against Ffh polypeptides.

In other embodiments of the invention there are provided methods for identifying compounds which bind to or otherwise interact with and inhibit or activate an activity of a polypeptide or polynucleotide of the invention comprising: contacting a polypeptide or polynucleotide of the invention with a compound to be screened under conditions to permit binding to or other interaction between the compound and the polypeptide or polynucleotide to assess the binding to or other interaction with the compound, such binding or interaction being associated with a second component capable of providing a detectable signal in response to the binding or interaction of the polypeptide or polynucleotide with the compound; and determining whether the compound binds to or otherwise interacts with and activates or inhibits an activity of the polypeptide or polynucleotide by detecting the presence or absence of a signal generated from the binding or interaction of the compound with the polypeptide or polynucleotide.

In accordance with yet another aspect of the invention, there are provided SRP agonists and antagonists, preferably bacteriostatic or bacteriocidal agonists and antagonists.

In a further aspect of the invention there are provided compositions comprising a SRP polynucleotide or a SRP polypeptide for administration to a cell or to a multicellular organism.

Various changes and modifications within the spirit and scope of the disclosed invention will become readily apparent to those skilled in the art from reading the following descriptions and from reading the other parts of the present disclosure.

GLOSSARY

The following definitions are provided to facilitate understanding of certain terms used frequently herein. Certain other definitions are provided elsewhere herein.

"Host cell" is a cell which has been transformed or transfected, or is capable of transformation or transfection by an exogenous polynucleotide sequence.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12(1): 387 (1984)), BLASTP, BLASTN, and FASTA (Atschul, S. F. et al., *J. Molec. Biol.* 215: 403–410 (1990). The BLAST X program is publicly available from NCBI and other sources (*BLAST Manual*, Altschul, S., et al., NCBI NLM NIH Bethesda, Mich. 20894; Altschul, S., et al., *J. Mol. Biol.* 215: 403–410 (1990). As an illustration, by a polynucleotide having a nucleotide sequence having at least, for example, 95% "identity" to a reference nucleotide sequence of SEQ ID NO:1 it is intended that the nucleotide sequence of the polynucleotide is identical to the reference sequence except that the polynucleotide sequence may include up to five point mutations per each 100 nucleotides of the reference nucleotide sequence of SEQ ID NO:1. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5 or 3 terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence of SEQ ID NO:2 is intended that the amino acid sequence of the polypeptide is identical to the reference sequence except that the polypeptide sequence may include up to five amino acid alterations per each 100 amino acids of the reference amino acid of SEQ ID NO:2. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein.

"Polynucleotide(s)" generally refers to any polyribonucleotide or polydeoxribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *PROTEINS— STRUCTURE AND MOLECULAR PROPERTIES,* 2nd Ed., T. E. Creighton, W. H. Freeman and Company, New York (1993) and Wold, F., Posttranslational Protein Modifications: Perspectives and Prospects, pgs. 1–12 in *POSTTRANSLATIONAL COVALENT MODIFICATION OF PROTEINS,* B. C. Johnson, Ed., Academic Press, New York (1983); Seifter et al., *Meth. Enzymol.* 182:626–646 (1990) and Rattan et al., *Protein Synthesis: Posttranslational Modifications and Aging,* Ann. N.Y. Acad. Sci. 663: 48–62 (1992). Polypeptides may be branched or cyclic, with or without branching. Cyclic, branched and branched circular polypeptides may result from post-translational natural processes and may be made by entirely synthetic methods, as well.

"Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

DETAILED DESCRIPTION OF THE INVENTION

The ribonucleoprotein, Signal Recognition Particle (hereinafter referred to as SRP), consists of a protein component known as Ffh and a ribonucleic acid component encoded by the ffs gene. SRP plays a key role in the targetting of nascent intrinsic cytoplasmic membrane proteins to the membrane and in the targetting of some soluble proteins to the periplasm in Gram-negative bacteria or to extra-cellular locations in Gram-positive bacteria. SRP is known to interact with the FtsY protein, the product of the ftsY gene, in eubacteria and also with hydrophobic regions of pre-secretory proteins and with hydrophobic regions of intrinsic membrane proteins. The interaction between SRP and FtsY results in reciprocal stimulation of the intrinsic guanosine triphosphate (GTP) hydrolytic activity of each protein. Loss of biological activity of either Ffh protein or FtsY protein is incompatible with bacterial cell survival.

The invention relates to novel SRP polypeptides and polynucleotides as described in greater detail below. In particular, the invention relates to polypeptides and polynucleotides of a novel Ffh of *Staphylococcus aureus*, which is related by amino acid sequence homology to Ffh polypeptide set forth in SEQ ID NO:2. The invention relates especially to Ffh having the nucleotide and amino acid sequences set out in Table 1, SEQ ID NO:1 and SEQ ID NO:2 respectively, and to the ffh nucleotide sequences of the DNA in the deposited strain and amino acid sequences encoded thereby. The invention also relates to the SRP RNA component, particularly in its protein binding form, and sequences from which such component is transcribed.

SRP RNA Component

Phylogenetic comparisons readily allow secondary structure modeling and the identification of a minimum consensus structure. Several ribonucleosides within the ffs sequence of eubacteria which have an impotant role in functioning of the SRP have been identified.

SRP Protein Component

The precise functional role of the protein involves recognition of and binding to ffs RNA, GTP, FtsY and hydrophobic regions of pre-secretory proteins and with hydrophobic regions of intrinsic membrane proteins. The interaction between SRP and FtsY results in reciprocal stimulation of the intrinsic guanosine triphosphate (GTP) hydrolytic activity of each protein.

The full length sequence encoding the intact SRP protein component can be obtained by probing a genomic library by for example in situ colony hybridization detailed in Maniatis et al. (infra) using a probe(s) generated based on the sequences given in SEQ ID NOS:1 and/or 2.

TABLE 1

SRP Polynucleotide and Polypeptide Sequences (A) Sequences from *Staphylococcus aureus* ffh polynucleotide sequence
[SEQ ID NO:1].
5'-ATGGCATTTGAAGGCTTATCAGAACGCCTGCAAGCGACGATGCAAAAAATGCGTGGTAAGGGTAAACTTA
CTGAAGCTGATATAAAGATAATGATGCGTGAAGTAAGATTAGCGTTATTTGAGGCTGACGTAAACTTTAA
AGTGGTAAAAGAATTTATTAAAACAGTATCAGAACGCGCATTAGGTTCCGATGTAATGCAATCATTAACA
CCAGGGCAACAAGTTATTAAAATAGTTCAAGATGAATTAACGAAGTTGATGGGTGGAGAAAATACATCGA
TTAATATGTCAAATAAACCACCTACTGTTGTTATGATGGTTGGTTTACAAGGTGCTGGTAAAACAACAAC
TGCAGGTAAATTAGCATTATTGATGCGTAAAAAATACAACAAAAAACCTATGTTAGTTGCAGCAGATATT
TATCGTCCAGCAGCGATAAATCAATTACAAACAGTAGGGAAACAAATTGATATTCCTGTATACAGTGAAG
GAGATCAAGTAAAGCCACAACAAATTGTAACTAATGCATTAAAACATGCTAAAGAAGAACATTTAGACTT
TGTAATCATTGATACAGCAGGTCGATTACACATCGATGAAGCATTGATGAACGAATTAAAAGAAGTAAAA
GAAATTGCTAAACCAAACGAAATTATGTTAGTTGTCGATTCAATGACGGGTCAAGATGCTGTCAATGTTG
CAGAATCTTTTGACGATCAACTTGATGTCACAGGTGTTACCTTAACTAAATTAGATGGTGATACCCGTGG
TGGTGCAGCTTTATCTATTCGT-3'

(B) Ffh polypeptide sequence deduced from the polynucleotide sequence in
this table [SEQ ID NO:2].
NH$_2$-MAFEGLSERLQATMQKMRGKGKLTEADIKIMMREVRLALFEADVNFKVVKEFIKTVSERALGSDVMQSLT
PGQQVIKIVQDELTKLMGGENTSINMSNKPPTVVMMVGLQGAGKTTTAGKLALLMRKKYNKKPMLVAADI
YRPAAINQLQTVGKQIDIPVYSEGDQVKPQQIVTNALKHAKEEHLDFVIIDTAGRLHIDEALMNELKEVK
EIAKPNEIMLVVDSMTGQDAVNVAESFDDQLDVTGVTLTKLDGDTRGGAALSIR-COOH (C) Polynucleotide sequence embodiments [SEQ ID NO:1].
X-(R$_1$)$_n$
ATGGCATTTGAAGGCTTATCAGAACGCCTGCAAGCGACGATGCAAAAAATGCGTGGTAAGGGTAAACTTA
CTGAAGCTGATATAAAGATAATGATGCGTGAAGTAAGATTAGCGTTATTTGAGGCTGACGTAAACTTTAA
AGTGGTAAAAGAATTTATTAAAACAGTATCAGAACGCGCATTAGGTTCCGATGTAATGCAATCATTAACA
CCAGGGCAACAAGTTATTAAAATAGTTCAAGATGAATTAACGAAGTTGATGGGTGGAGAAAATACATCGA
TTAATATGTCAAATAAACCACCTACTGTTGTTATGATGGTTGGTTTACAAGGTGCTGGTAAAACAACAAC
TGCAGGTAAATTAGCATTATTGATGCGTAAAAAATACAACAAAAAACCTATGTTAGTTGCAGCAGATATT
TATCGTCCAGCAGCGATAAATCAATTACAAACAGTAGGGAAACAAATTGATATTCCTGTATACAGTGAAG
GAGATCAAGTAAAGCCACAACAAATTGTAACTAATGCATTAAAACATGCTAAAGAAGAACATTTAGACTT
TGTAATCATTGATACAGCAGGTCGATTACACATCGATGAAGCATTGATGAACGAATTAAAAGAAGTAAAA
GAAATTGCTAAACCAAACGAAATTATGTTAGTTGTCGATTCAATGACGGGTCAAGATGCTGTCAATGTTG
CAGAATCTTTTGACGATCAACTTGATGTCACAGGTGTTACCTTAACTAAATTAGATGGTGATACCCGTGG
TGGTGCAGCTTTATCTATTCGT-(R$_2$)$_n$-Y (D) Polypeptide sequence embodiments [SEQ ID NO:2].
X-(R$_1$)$_n$-
MAFEGLSERLQATMQKMRGKGKLTEADIKIMMREVRLALFEADVNFKVVKEFIKTVSERALGSDVMQSLT
PGQQVIKIVQDELTKLMGGENTSINMSNKPPTVVMMVGLQGAGKTTTAGKLALLMRKKYNKKPMLVAADI
YRPAAINQLQTVGKQIDIPVYSEGDQVKPQQIVTNALKHAKEEHLDFVIIDTAGRLHIDEALMNELKEVK
EIAKPNEIMLVVDSMTGQDAVNVAESFDDQLDVTGVTLTKLDGDTRGGAALSIR -(R$_2$)$_n$-Y (E) Sequences from *Staphylococcus aureus* SRP RNA gene ffs [SEQ ID NO:3].
5'-AACAATGCCGTTTCAATATAATATTTCAAAACATCTTGCAAATGAATTTAAATTTACCGACTTCTCAAGA
CGTCGTATAAAGTAAACAATGATATAAATGATTTATACTTGCAATTAACTATTNAAATATAGTAATATAT
ATCTTTCCGTGCTAGGTGGGAGGTAGCGGTTCCCTGTACTCGAAATCCGCTTTATGCGAGGCTTAATTC
CTTTGTTGAGGCCGTATTTTTGCGAAGTCTGCCCAAAGCACGTAGTGTTTGAAGATTTCGGTCCT-3'

TABLE 1-continued

SRP Polynucleotide and Polypeptide Sequences (F) Polynucleotide sequence embodiments [SEQ ID NO:3].
X-(R$_1$)$_n$
AACAATGCCGTTTCAATATAATATTTCAAAACATCTTGCAAATGAATTTAAATTTACCGACTTCTCAAGA
CGTCGTATAAAGTAAACAATGATATAAATGATTTATACTTGCAATTAACTATTNAAATATAGTAATATAT
ATCTTTCCGTGCTAGGTGGGAGGTAGCGGTTCCCTGTACTCGAAATCCGCTTTATGCGAGGCTTAATTC
CTTTGTTGAGGCCGTATTTTTGCGAAGTCTGCCCAAAGCACGTAGTGTTTGAAGATTTCGGTCCT-(R$_2$)$_n$-Y

Polypeptides of the Invention

The polypeptides of the invention include the polypeptide of Table 1 [SEQ ID NO:2] (in particular the mature polypeptide) as well as polypeptides and fragments, particularly those which have the biological activity of Ffh, and also those which have at least 70% identity to the polypeptide of Table 1 [SEQ ID NO:2] or the relevant portion, preferably at least 80% identity to the polypeptide of Table 1 [SEQ ID NO:2], and more preferably at least 90% similarity (more preferably at least 90% identity) to the polypeptide of Table 1 [SEQ ID NO:2] and still more preferably at least 95% similarity (still more preferably at least 95% identity) to the polypeptide of Table 1 [SEQ ID NO:2] and also include portions of such polypeptides with such portion of the polypeptide generally containing at least 30 amino acids and more preferably at least 50 amino acids.

The invention also includes polypeptides of the formula set forth in Table 1 (D) [SEQ ID NO:2] wherein, at the amino terminus, X is hydrogen, and at the carboxyl terminus, Y is hydrogen or a metal, R$_1$ and R$_2$ is any amino acid residue, and n is an integer between 1 and 1000 or zero. Any stretch of amino acid residues denoted by either R group, where R is reater than 1, may be either a heteropolymer or a homopolymer, preferably a heteropolymer.

A fragment is a variant polypeptide having an amino acid sequence that entirely is the same as part but not all of the amino acid sequence of the aforementioned polypeptides. As with Ffh polypeptides fragments may be "free-standing," or comprised within a larger polypeptide of which they form a part or region, most preferably as a single continuous region, a single larger polypeptide.

Preferred fragments include, for example, truncation polypeptides having a portion of the amino acid sequence of Table b 1[SEQ ID NO:2], or of variants thereof, such as a continuous series of residues that includes the amino terminus, or a continuous series of residues that includes the carboxyl terminus. Degradation forms of the polypeptides of the invention in a host cell, particularly a *Staphylococcus aureus*, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Also preferred are biologically active fragments which are those fragments that mediate activities of Ffh, including those with a similar activity or an improved activity, or with a decreased undesirable activity. Also included are those fragments that are antigenic or immunogenic in an animal, especially in a human. Particularly preferred are fragments comprising receptors or domains of enzymes that confer a function essential for viability of *Staphylococcus aureus* or the ability to initiate, or maintain cause disease in an individual, particularly a human.

Variants that are fragments of the polypeptides of the invention may be employed for producing the corresponding full-length polypeptide by peptide synthesis; therefore, these variants may be employed as intermediates for producing the full-length polypeptides of the invention.

Polynucleotides of the Invention

Another aspect of the invention relates to isolated polynucleotides, including the full length gene, that encode the Ffh polypeptide having a deduced amino acid sequence of Table 1 [SEQ ID NO:2] and polynucleotides closely related thereto and variants thereof.

Using the information provided herein, such as a polynucleotide sequence set out in SEQ ID NOS:1 or 3, a polynucleotide of the invention encoding SRP polypeptide or RNA (such as that transcribed from SEQ ID NO:3) may be obtained using standard cloning and screening methods, such as those for cloning and sequencing chromosomal DNA fragments from bacteria using *Staphylococcus aureus* WCUH 29 cells as starting material, followed by obtaining a full length clone. For example, to obtain a polynucleotide sequence of the invention, such as a sequence given in SEQ ID NOS:1 or 3, typically a library of clones of chromosomal DNA of *Staphylococcus aureus* WCUH 29 in *E.coli* or some other suitable host is probed with a radiolabeled oligonucleotide, preferably a 17-mer or longer, derived from a partial sequence. Clones carrying DNA identical to that of the probe can then be distinguished using stringent conditions. By sequencing the individual clones thus identified with sequencing primers designed from the original sequence it is then possible to extend the sequence in both directions to determine the full gene sequence. Conveniently, such sequencing is performed using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, New York (1989). (see in particular Screening By Hybridization 1.90 and Sequencing Denatured Double-Stranded DNA Templates 13.70). Illustrative of the invention, the polynucleotides set out in Table 1 [SEQ ID NO:1] were discovered in a DNA library derived from *Staphylococcus aureus*

Certain DNA sequences set out in Table 1 [SEQ ID NO:1] contains an open reading frame encoding a protein having about the number of amino acid residues set forth in Table 1 [SEQ ID NO:2] with a deduced molecular weight that can be calculated using amino acid residue molecular weight values well known in the art.

Ffh of the invention is structurally related to other proteins of the Ffh family, as shown by the results of sequencing the DNA encoding Ffh of the deposited strain. The protein exhibits greatest homology to *B.subtilis* protein among known proteins. Ffh of Table 1 [SEQ ID NO:2] has significant identity and similarity over its entire length with the amino acid sequence of *B.subtilis* Ffh polypeptide.

The invention provides a polynucleotide sequence identical over its entire length to the coding sequence in Table b 1[SEQ ID NO:1]. Also provided by the invention is the coding sequence for the mature polypeptide or a fragment thereof, by itself as well as the coding sequence for the mature polypeptide or a fragment in reading frame with other coding sequence, such as those encoding a leader or secretory sequence, a pre-, or pro- or prepro-protein sequence. The polynucleotide may also contain non-coding sequences, including for example, but not limited to non-coding 5' and 3' sequences, such as the transcribed, non-translated sequences, termination signals, ribosome binding sites, sequences that stabilize mRNA, introns, polyadenylation signals, and additional coding sequence which encode additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821–824 (1989), or an HA tag (Wilson et al., *Cell* 37: 767 (1984). Polynucleotides of the invention also include, but are not limited to, polynucleotides comprising a structural gene and its naturally associated sequences that control gene expression.

A preferred embodiment of the invention is a polynucleotide set forth in SEQ ID NO:1 of Table 1 which encodes the Ffh polypeptide.

The invention also includes polynucleotides of the formula set forth in Table 1 (C)[SEQ ID NO:1 and (F)[SEQ ID NO:3] wherein, at the 5' end of the molecule, X is hydrogen, and at the 3' end of the molecule, Y is hydrogen or a metal, $R_1$ and $R_2$ is any nucleic acid residue, and n is an integer between 1 and 3000 or zero. Any stretch of nucleic acid residues denoted by either R group, where R is greater than 1, may be either a heteropolymer or a homopolymer, preferably a heteropolymer. A preferred embodiment for the sequence set forth in Table 1 (F) [SEQ ID NO:3] has $R_1$ or $R_2$ being between 1 and 10 or 1 and 20, and especially being 1 or 3. The invention also provides RNA transcribed from such polynucleotides, particularly RNAs that bind an Ffh polypeptide.

The term "polynucleotide encoding a polypeptide" as used herein encompasses polynucleotides that include a sequence encoding a polypeptide of the invention, particularly a bacterial polypeptide and more particularly a polypeptide of the *Staphylococcus aureus* Ffh having the amino acid sequence set out in Table 1 [SEQ ID NO:2]. The term also encompasses polynucleotides that include a single continuous region or discontinuous regions encoding the polypeptide (for example, interrupted by integrated phage or an insertion sequence or editing) together with additional regions, that also may contain coding and/or non-coding sequences.

The invention further relates to variants of the polynucleotides described herein that encode for variants of the polypeptide having the deduced amino acid sequence of Table b 1[SEQ ID NO:2]. Variants that are fragments of the polynucleotides of the invention may be used to synthesize full-length polynucleotides of the invention.

In addition to the standard A, G, C, T/U representations for nucleic acid bases, the term "N" is also used. "N" means that any of the four DNA or RNA bases may appear at such a designated position in the DNA or RNA sequence, except that, in preferred embodiments, N can not be a base that when taken in combination with adjacent nucleotide positions, when read in the correct reading frame, would have the effect of generating a premature termination codon in such reading frame.

Further particularly preferred embodiments are polynucleotides encoding Ffh variants, that have the amino acid sequence of Ffh polypeptide of Table b 1[SEQ ID NO:2] in which several, a few, 5 to 10, 1 to 5, 1 to 3, 2, 1 or no amino acid residues are substituted, deleted or added, in any combination. Especially preferred among these are silent substitutions, additions and deletions, that do not alter the properties and activities of SRP.

Further preferred embodiments of the invention are polynucleotides that are at least 50%, 60% or 70% identical over their entire length to a polynucleotide encoding Ffh polypeptide having an amino acid sequence set out in Table 1 [SEQ ID NO:2], and polynucleotides that are complementary to such polynucleotides. Alternatively, most highly preferred are polynucleotides that comprise a region that is at least 80% identical over its entire length to a polynucleotide encoding Ffh polypeptide of the deposited strain and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments of the invention are polynucleotides that are at least 50%, 60% or 70% identical over their entire length to an Ffh polynucleotide having a nucleotide sequence set out in SEQ ID NO:3 and polynucleotides that are complementary to such polynucleotides. Alternatively, most highly preferred are polynucleotides that comprise a region that is at least 80% identical over its entire length to an Ffh polynucleotide of the deposited strain and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred. It is especially preferred that these polynucleotides be RNAs, especially RNAs that bind Ffh polypeptides.

Preferred embodiments are polynucleotides that encode polypeptides that retain substantially the same biological function or activity as the mature polypeptide encoded by the DNA of Table 1 [SEQ ID NO:1 ] or as the SRP RNA component transcribed by the DNA of SEQ ID NO:3.

The invention further relates to polynucleotides that hybridize to the herein above-described sequences. In this regard, the invention especially relates to polynucleotides that hybridize under stringent conditions to the herein above-described polynucleotides. As herein used, the terms "stringent conditions" and "stringent hybridization conditions" mean hybridization will occur only if there is at least 95% and preferably at least 97% identity between the sequences. An example of stringent hybridization conditions is overnight incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml denatured, sheared salmon sperm DNA, followed by washing the hybridization support in 0.1×SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein.

The invention also provides a polynucleotide consisting essentially of a polynucleotide sequence obtainable by screening an appropriate library containing the complete gene for a polynucleotide sequence set forth in SEQ ID NO:1 or SEQ ID NO:3 under stringent hybridization conditions with a probe having the sequence of said polynucleotide sequence set forth in SEQ ID NO:1 or SEQ ID NO:3 respectively or a fragment thereof; and isolating said DNA sequence. Fragments useful for obtaining such a polynucleotide include, for example, probes and primers described elsewhere herein.

As discussed herein regarding polynucleotide assays of the invention, for instance, polynucleotides of the invention as discussed above, may be used as a hybridization probe for RNA, cDNA and genomic DNA to isolate full-length cDNAs and genomic clones encoding SRP and to isolate cDNA and genomic clones of other genes that have a high sequence similarity to the SRP gene. Such probes generally will comprise at least 15 bases. Preferably, such probes will have at least 30 bases and may have at least 50 bases. Particularly preferred probes will have at least 30 bases and will have 50 bases or less.

Polynucleotides of the invention that are oligonucleotides derived from the sequences of SEQ ID NOS:1 and/or 2 and/or 3 may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that may encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

Further Description and Definitions

The coding region of the SRP gene may be isolated, for example, by screening using a deposit containing a *Staphylococcus aureus* WCUH 29 strain which has been deposited with the National Collections of Industrial and Marine Bacteria Ltd. (herein "NCIMB"), 23 St. Machar Drive, Aberdeen AB21 RY, Scotland on Sep. 11, 1995 and assigned NCIMB Deposit No. 40771. It was referred to as *Staphylococcus aureus* WCUH29 on deposit. The *Staphylococcus aureus* strain deposit is referred to herein as "the deposited strain" or as "the DNA of the deposited strain."

The deposited strain contains the full length SRP gene. The sequence of the polynucleotides contained in the deposited strain, as well as the amino acid sequence of the polypeptide encoded thereby, are controlling in the event of any conflict with any description of sequences herein.

The deposit of the deposited strain has been made under the terms of the Budapest Treaty on the International Recognition of the Deposit of Micro-organisms for Purposes of Patent Procedure. The strain will be irrevocably and without restriction or condition released to the public upon the issuance of a patent. The deposited strain is provided merely as convenience to those of skill in the art and is not an admission that a deposit is required for enablement, such as that required under 35 U.S.C. §112.

A license may be required to make, use or sell the deposited strain, and compounds derived therefrom, and no such license is hereby granted.

The nucleotide sequences disclosed herein can also be obtained by synthetic chemical techniques known in the art or can be obtained from *S. aureus* WCUH 29 by probing a DNA preparation with probes constructed from the particular sequences disclosed herein. Alternatively, oligonucleotides derived from a disclosed sequence can act as PCR primers in a process of PCR-based cloning of the sequence from a bacterial genomic source. It is recognized that such sequences will also have utility in diagnosis of the type of infection the pathogen has attained.

A polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the polypeptide may be identical to the coding sequence shown or may be a different coding sequence which coding sequence, as a result of the redundancy or degeneracy of the genetic code, encoding the same polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention therefore includes polynucleotides, wherein the coding sequence for the mature polypeptide may be fused in the same reading frame to a olynucleotide sequence which aids in expression and secretion of a polypeptide from a host cell, for example, a leader sequence which functions as a secretory sequence for controlling transport of a polypeptide from the cell. The polypeptide having a leader sequence is a preprotein and may have the leader sequence cleaved by the host cell to form the mature form of the polypeptide. The polynucleotides may also encode for a proprotein which is the mature protein plus additional 5' amino acid residues. A mature protein having a prosequence is a proprotein and is an inactive form of the protein. Once the prosequence is cleaved an active mature protein remains.

Thus, for example, the polynucleotide of the present invention may encode for a mature protein, or for a protein having a prosequence or for a protein having both a prosequence and a presequence (leader sequence). Further, the amino acid sequences provided herein show a methionine residue at the NH$_2$-terminus. It is appreciated, however, that during post-translational modification of the peptide, this residue may be deleted. Accordingly, this invention contemplates the use of both the methionine-containing and the methionineless amino terminal variants of each protein disclosed herein.

The polynucleotides of the present invention may also have the coding sequence fused in frame to a marker sequence at either the 5' or 3' terminus of the gene which allows for purification of the polypeptide of the present invention. The marker sequence may be a hexa-histidine tag supplied by the pQE series of vectors (supplied commercially by Quiagen Inc.) to provide for purification of the polypeptide fused to the marker in the case of a bacterial host. Alternatively the maltose binding protein (MBP) fusion system may be employed. In this system the gene of interest is fused the malE gene encoding the MBP (supplied by New England BioLabs). The fusion product is purified in a one step procedure based on the MBP affinity for maltose. A pre-engineered Xa cleavage site allows for efficient removal of the MBP component from the gene product of interest.

In order to facilitate understanding of the following example certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on an agarose gel to isolate the desired fragment. Size separation of the cleaved fragments is generally performed using a 1% percent agarose gel.

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., supra. p. 146). Unless otherwise provided, ligation may be accomplished using known buffers and conditions with 10 units to T4 DNA ligase ("ligase") per 0.5 μg of approximately equimolar amounts of the DNA fragments to be ligated.

The polypeptides and polynucleotides of the present invention are preferably provided in an isolated form, and preferably are purified to homogeneity.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A "double-stranded DNA molecule" refers to the polymeric form of deoxyribonucleotides (bases adenine, guanine, thymine, or cytosine) in a double-stranded helix, both relaxed and supercoiled. This term refers only to the primary and secondary tructure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence of" or a "nucleotide sequence encoding" a particular protein, is a DNA sequence which is transcribed and translated into a polypeptide when placed under the control of appropriate regulatory sequences.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by a translation start codon (e.g., ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain the −10 and −35 consensus sequences.

DNA "control sequences" refers collectively to promoter sequences, ribosome binding sites, polyadenylation signals, transcription termination sequences, upstream regulatory domains, enhancers, and the like, which collectively provide for the expression (i.e., the transcription and translation) of a coding sequence in a host cell.

A control sequence "directs the expression" of a coding sequence in a cell when RNA polymerase will bind the promoter sequence and transcribe the coding sequence into mRNA, which is then translated into the polypeptide encoded by the coding sequence.

A "host cell" is a cell which has been transformed or transfected, or is capable of transformation or transfection by an exogenous DNA sequence.

A cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cell containing the exogenous DNA.

A "clone" is a population of cells derived from a single cell or common ancestor by mitosis. A "cell line" is a clone of a primary cell that is capable of stable growth in vitro for many generations.

A "heterologous" region of a DNA construct is an identifiable segment of DNA within or attached to another DNA molecule that is not found in association with the other molecule in nature.

Preparation of the SRP Protein Component

The present invention also relates to vectors which include polynucleotides of the present invention, host cells which are genetically engineered with vectors of the invention and the production of polypeptides of the invention by recombinant techniques.

In accordance with yet a further aspect of the present invention, there is therefore provided a process for producing the polypeptide of the invention by recombinant techniques by expressing a polynucleotide encoding said polypeptide in a host and recovering the expressed product. Alternatively, the polypeptides of the invention can be synthetically produced by conventional peptide synthesizers.

Host cells are genetically engineered (transduced or transformed or transfected) with the vectors of this invention which may be, for example, a cloning vector or an expression vector. The vector may be, for example, in the form of a plasmid, a cosmid, a phage, etc. The engineered host cells can be cultured in conventional nutrient media modified as appropriate for activating promoters, selecting transformants or amplifying the genes. The culture conditions, such as temperature, pH and the like, are those previously used with the host cell selected for expression, and will be apparent to the ordinarily skilled artisan.

Suitable expression vectors include chromosomal, non-chromosomal and synthetic DNA sequences, e.g., bacterial plasmids; phage DNA; baculovirus; yeast plasmids; vectors derived from combinations of plasmids and phage DNA. However, any other vector may be used as long as it is replicable and viable in the host.

For recombinant production, host cells can be genetically engineered to incorporate expression systems or portions thereof or polynucleotides of the invention. Introduction of a polynucleotide into the host cell can be effected by methods described in many standard laboratory manuals, such as Davis et al., BASIC METHODS IN MOLECULAR BIOLOGY, (1986) and Sambrook et al., MOLECULAR CLONING: A LABORATORY MANUAL, 2nd Ed., Cold Spring Harbor Laboratory Press, Cold Spring Harbor, N.Y. (1989), such as, calcium phosphate transfection, DEAE-dextran mediated transfection, transvection, microinjection, cationic lipid-mediated transfection, electroporation, transduction, scrape loading, ballistic introduction and infection.

Representative examples of appropriate hosts include bacterial cells, such as streptococci, staphylococci, enterococci E. coli, streptomyces and Bacillus subtilis cells; fungal cells, such as yeast cells and Aspergillus cells; insect cells such as Drosophila S2 and Spodoptera Sf9 cells; animal cells such as CHO, COS, HeLa, C127, 3T3, BHK, 293 and Bowes melanoma cells; and plant cells.

A great variety of expression systems can be used to produce the polypeptides of the invention. Such vectors include, among others, chromosomal, episomal and virus-derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., MOLECULAR CLONING, A LABORATORY MANUAL, (supra).

The appropriate DNA sequence may be inserted into the vector by a variety of procedures. In general, the DNA sequence is inserted into an appropriate restriction endonuclease site(s) by procedures known in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in eukaryotic or prokaryotic cells or their viruses. The expression vector may also contains a ribosome binding site for translation initiation and/or a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. The polypeptides of the present invention can be expressed using, for example, the E. coli tac promoter or the protein A gene (spa) promoter and signal sequence. Leader sequences can be removed by the bacterial host in post-translational processing. See, e.g., U.S. Pat. Nos. 4,431,739; 4,425,437; 4,338,397. Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the coding sequences may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

The vector containing the appropriate DNA sequence as hereinabove described, as well as an appropriate promoter or control sequence, may be employed to transform an appropriate host to permit the host to express the protein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pET-3 vectors (Stratagene), pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: pBlueBacIII (Invitrogen), pWLNEO, pSV2CAT, pOG44, pXT1, pSG (Stratagene) pSVK3, pBPV, pMSG, pSVL (Pharmacia).

However, any other plasmid or vector may be used as long as they are replicable and viable in the host.

Examples of recombinant DNA vectors for cloning and host cells which they can transform include the bacteriophage λ (E. coli), pBR322 (E. coli), pACYC177 (E. coli), pKT230 (gram-negative bacteria), pGV1106 (gram-negative bacteria), pLAFR1 (gram-negative bacteria), pME290 (non-E. coli gram-negative bacteria), pHV 14 (E. coli and Bacillus subtilis), pBD9 (Bacillus), pIJ61 (Streptomyces), pUC6 (Streptomyces), YIp5 (Saccharomyces), a baculovirus insect cell system, YCp19 (Saccharomyces). See, generally, "DNA Cloning" : Vols. I & II, Glover et al. ed. IRL Press Oxford (1985) (1987) and; T. Maniatis et al. ("Molecular Cloning" Cold Spring Harbor Laboratory (1982).

In some cases, it may be desirable to add sequences which cause the secretion of the polypeptide from the host organism, with subsequent cleavage of the secretory signal.

Polypeptides can be expressed in host cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well known to those skilled in the art.

Depending on the expression system and host selected, the polypeptide of the present invention may be produced by growing host cells transformed by an expression vector described above under conditions whereby the polypeptide of interest is expressed. The polypeptide is then isolated from the host cells and purified. If the expression system secretes the polypeptide into growth media, the polypeptide can be purified directly from the media. If the polypeptide is not secreted, it is isolated from cell lysates or recovered from the cell membrane fraction. Where the polypeptide is localized to the cell surface, whole cells or isolated membranes can be used as an assayable source of the desired gene product. Polypeptide expressed in bacterial hosts such as E. coli may require isolation from inclusion bodies and refolding. Where the mature protein has a very hydrophobic region which leads to an insoluble product of overexpression, it may be desirable to express a truncated protein in which the hydrophobic region has been deleted. The selection of the appropriate growth conditions and recovery methods are within the skill of the art.

The polypeptide can be recovered and purified from recombinant cell cultures by methods including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

Depending upon the host employed in a recombinant production procedure, the polypeptides of the present invention may be glycosylated or may be non-glycosylated. Polypeptides of the invention may also include an initial methionine amino acid residue.

Preparation of the SRP RNA Component

The SRP RNA molecules are prepared by run-off in vitro transcription using T7 RNA polymerase as according to standard conditions usually as recommended by the supplier, e.g., Promega. The plasmid is linearized with an appropriate restriction enzyme generating a linear dsDNA comprising the full length gene encoding the SRP RNA. The RNA is purified either from a preparative denaturing acrylamide gel or is precipitated prior to use in in vitro cleavage assays. The RNA can also be prepared by automated synthesis.

Antagonists and Agonists—Assays and Molecules

This invention provides a method of screening drugs to identify those which interfere with the RNA portion, the protein portion and/or the intact RNA/protein complex of the SRP described herein, which method comprises measuring the interference of the activity of the protein and/or RNA by a test drug. For example since the RNA portion selected has a binding activity for Ffh polypeptide, after suitable purification and formulation the activity of the RNA can be followed by its ability to convert its natural or synthetic RNA substrates. By incorporating different chemically synthesized test compounds or natural products into such an assay of enzymatic activity one is able to detect those additives which compete with the natural or synthetic substrate or otherwise inhibit enzymatic activity.

Polypeptides of the invention may also be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., *Current Protocols in Immunology* 1(2): Chapter 5 (1991).

The invention also provides a method of screening compounds to identify those which enhance (agonist) or block (antagonist) the action of SRP polypeptides or polynucleotides, particularly those compounds that are bacteriostatic and/or bacteriocidal. The method of screening may involve high-throughput techniques. For example, to screen for agonists or antagonists, a synthetic reaction mix, a cellular compartment, such as a membrane, cell envelope or cell wall, or a preparation of any thereof, comprising Ffh polypeptide and a labeled substrate or ligand of such polypeptide is incubated in the absence or the presence of a candidate molecule that may be a SRP agonist or antagonist. The ability of the candidate molecule to agonize or antagonize the Ffh polypeptide is reflected in decreased binding of the labeled ligand or decreased production of product from such substrate. Molecules that bind gratuitously, i.e., without inducing the effects of Ffh polypeptide are most likely to be good antagonists. Molecules that bind well and increase the rate of product production from substrate are agonists. Detection of the rate or level of production of product from substrate may be enhanced by using a reporter system. Reporter systems that may be useful in this regard include but are not limited to colorimetric labeled substrate converted into product, a reporter gene that is responsive to changes in SRP polynucleotide or polypeptide activity, and binding assays known in the art.

Another example of an assay for SRP antagonists is a competitive assay that combines SRP and a potential antagonist with SRP-binding molecules, recombinant SRP binding molecules, natural substrates or ligands, or substrate or ligand mimetics, under appropriate conditions for a competitive inhibition assay. SRP can be labeled, such as by radioactivity or a colorimetric compound, such that the number of SRP molecules bound to a binding molecule or converted to product can be determined accurately to assess the effectiveness of the potential antagonist.

Potential antagonists include small organic molecules, peptides, polypeptides and antibodies that bind to a polynucleotide or polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing SRP-induced activities, thereby preventing the action of SRP by excluding SRP from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, *J. Neurochem.* 56: 560 (1991); *OLIGODEOXYNUCLEOTIDES AS ANTISENSE INHIBITORS OF GENE EXPRESSION*, CRC Press, Boca Raton, Fla. (1988), for a description of these molecules). Preferred potential antagonists include compounds related to and variants of SRP.

Each of the DNA sequences provided herein may be used in the discovery and development of antibacterial compounds. The encoded protein, upon expression, can be used as a target for the screening of antibacterial drugs. Additionally, the DNA sequences encoding the amino terminal regions of the encoded protein or Shine-Delgarno or other translation facilitating sequences of the respective mRNA can be used to construct antisense sequences to control the expression of the coding sequence of interest.

The invention also provides the use of the polypeptide, polynucleotide or inhibitor of the invention to interfere with the initial physical interaction between a pathogen and mammalian host responsible for sequelae of infection. In particular the molecules of the invention may be used: in the prevention of adhesion of bacteria, in particular gram positive bacteria, to mammalian extracellular matrix proteins on in-dwelling devices or to extracellular matrix proteins in wounds; to block SRP protein-mediated mammalian cell invasion by, for example, initiating phosphorylation of mammalian tyrosine kinases (Rosenshine et al., *Infect. Immun.* 60:2211 (1992); to block bacterial adhesion between mammalian extracellular matrix proteins and bacterial Ffh proteins that mediate tissue damage and; to block the normal progression of pathogenesis in infections initiated other than by the implantation of in-dwelling devices or by other surgical techniques.

The antagonists and agonists of the invention may be employed, for instance, to inhibit and treat disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhoea, splenic absces, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric absces, toxic shock syndrome), skin (e.g., impetigo, folliculitis, cutaneous abscesses, cellulitis, wound infection, bacterial myositis) bone and joint (e.g., septic arthritis, osteomyelitis).

HTP Screening Strategies

HTS strategy will be to measure the hydrolysis of GTP by measuring the accumulation of phosphate.

Diagnostic Assays

This invention is also related to the use of the SRP polynucleotides of the invention for use as diagnostic reagents. Detection of SRP in a eukaryote, particularly a mammal, and especially a human, will provide a diagnostic method for diagnosis of a disease. Eukaryotes (herein also "individual(s)"), particularly mammals, and especially humans, infected with an organism comprising the SRP gene may be detected at the nucleic acid level by a variety of techniques.

Nucleic acids for diagnosis may be obtained from an infected individual's cells and tissues, such as bone, blood, muscle, cartilage, and skin. Genomic DNA may be used directly for detection or may be amplified enzymatically by using PCR or other amplification technique prior to analysis. RNA or cDNA may also be used in the same ways. Using amplification, characterization of the species and strain of prokaryote present in an individual, may be made by an analysis of the genotype of the prokaryote gene. Deletions and insertions can be detected by a change in size of the amplified product in comparison to the genotype of a reference sequence. Point mutations can be identified by hybridizing amplified DNA to labeled SRP polynucleotide sequences. Perfectly matched sequences can be distinguished from mismatched duplexes by RNase digestion or by differences in melting temperatures. DNA sequence differences may also be detected by alterations in the electrophoretic mobility of the DNA fragments in gels, with or without denaturing agents, or by direct DNA sequencing. See, e.g., Myers et al., *Science*, 230: 1242 (1985). Sequence changes at specific locations also may be revealed by nuclease protection assays, such as RNase and S1 protection or a chemical cleavage method. See, e.g., Cotton et al., *Proc. Natl. Acad. Sci., USA*, 85: 4397–4401 (1985).

Cells carrying mutations or polymorphisms in the gene of the invention may also be detected at the DNA level by a variety of techniques, to allow for serotyping, for example. For example, RT-PCR can be used to detect mutations. It is particularly preferred to used RT-PCR in conjunction with automated detection systems, such as, for example, GeneScan. RNA or cDNA may also be used for the same purpose, PCR or RT-PCR. As an example, PCR primers complementary to a nucleic acid encoding SRP can be used to identify and analyze mutations. Examples of representative primers are shown in the Examples. The invention further provides these primers with 1, 2, 3 or 4 nucleotides removed from the 5' and/or the 3' end. These primers may be used for, among other things, amplifying SRP DNA isolated from a sample derived from an individual. The primers may be used to amplify the gene isolated from an infected individual such that the gene may then be subject to various techniques for elucidation of the DNA sequence. In this way, mutations in the DNA sequence may be detected and used to diagnose infection and to serotype and/or classify the infectious agent.

The invention further provides a process for diagnosing, disease, preferably bacterial infections, more preferably infections by *Staphylococcus aureus*, and most preferably disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhoea, splenic absces, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric absces, toxic shock syndrome), skin (e.g., impetigo, folliculitis, cutaneous abscesses, cellulitis, wound infection, bacterial myositis) bone and joint (e.g., septic arthritis, osteomyelitis), comprising determining from a sample derived from an individual a increased level of expression of polynucleotide having the sequence of Table 1 [SEQ ID NO:1]. Increased or decreased expression of SRP polynucleotide can be measured using any on of the methods well known in the art for the quantitation of polynucleotides, such as, for example, amplification, PCR, RT-PCR, SRProtection, Northern blotting and other hybridization methods.

In addition, a diagnostic assay in accordance with the invention for detecting over-expression of Ffh protein compared to normal control tissue samples may be used to detect the presence of an infection, for example. Assay techniques that can be used to determine levels of a Ffh protein, in a sample derived from a host are well-known to those of skill in the art. Such assay methods include radioimmunoassays, competitive-binding assays, Western Blot analysis and ELISA assays.

Antibodies

The polypeptides of the invention or variants thereof, or cells expressing them can be used as an immunogen to produce antibodies immunospecific for such polypeptides. "Antibodies" as used herein includes monoclonal and polyclonal antibodies, chimeric, single chain, simianized antibodies and humanized antibodies, as well as Fab fragments, including the products of an Fab immunolglobulin expression library.

The Fab fragment may also be prepared from its parent monoclonal antibody by enzyme treatment, for example using papain to cleave the Fab portion from the Fc portion.

Antibodies generated against the polypeptides of the invention can be obtained by administering the polypeptides or epitope-bearing fragments, analogues or cells to an animal, preferably a nonhuman, using routine protocols. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide. For preparation of monoclonal antibodies, any technique known in the art that provides antibodies produced by continuous cell line cultures can be used. Examples include various techniques, such as those in Kohler, G. and Milstein, C., *Nature* 256: 495–497 (1975); Kozbor et al., *Immunology Today* 4: 72 (1983); Cole et al., pg. 77–96 in *MONOCLONAL ANTIBODIES AND CANCER*

*THERAPY*, Alan R. Liss, Inc. (1985), )), and the EBV-hybridoma technique to produce human monoclonal antibodies (Cole, et al., 1985, in Monoclonal Antibodies and Cancer Therapy, Alan R. Liss, Inc., pp. 77–96).

The hybridomas are screened to select a cell line with high binding affinity and favorable cross reaction with other staphylococcal species using one or more of the original polypeptide and/or the fusion protein. The selected cell line is cultured to obtain the desired Mab.

Techniques for the production of single chain antibodies (U.S. Pat. No. 4,946,778) can be adapted to produce single chain antibodies to polypeptides of this invention. Also, transgenic mice, or other organisms such as other mammals, may be used to express humanized antibodies.

Alternatively phage display technology may be utilized to select antibody genes with binding activities towards the polypeptide either from repertoires of PCR amplified v-genes of lymphocytes from humans screened for possessing anti-Ffh or from naive libraries (McCafferty, J. et al., (1990), Nature 348, 552–554; Marks, J. et al., (1992) Biotechnology 10, 779–783). The affinity of these antibodies can also be improved by chain shuffling (Clackson, T. et al., (1991) Nature 352, 624–628).

The antibody should be screened again for high affinity to the polypeptide and/or fusion protein.

As mentioned above, a fragment of the final antibody may be prepared.

The antibody may be either intact antibody of $M_r$ approx 150,000 or a derivative of it, for example a Fab fragment or a Fv fragment as described in Skerra, A and Pluckthun, A., *Science* 240:1038–1040 (1988). If two antigen binding domains are present each domain may be directed against a different epitope—termed 'bispecific' antibodies.

If two antigen binding domains are present each domain may be directed against a different epitope—termed 'bispecific' antibodies.

In particular derivatives which are slightly longer or slightly shorter than the native protein or polypeptide fragment of the present invention may be used. In addition, polypeptides in which one or more of the amino acid residues are modified may be used. Such peptides may, for example, be prepared by substitution, addition, or rearrangement of amino acids or by chemical modification thereof. All such substitutions and modifications are generally well known to those skilled in the art of peptide chemistry.

The above-described antibodies may be employed to isolate or to identify clones expressing the polypeptides to purify the polypeptides by affinity chromatography.

Thus, among others, antibodies against Ffh- polypeptide may be employed to treat infections, particularly bacterial infections and especially disease, such as, infections of the upper respiratory tract (e.g., otitis media, bacterial tracheitis, acute epiglottitis, thyroiditis), lower respiratory (e.g., empyema, lung abscess), cardiac (e.g., infective endocarditis), gastrointestinal (e.g., secretory diarrhoea, splenic absces, retroperitoneal abscess), CNS (e.g., cerebral abscess), eye (e.g., blepharitis, conjunctivitis, keratitis, endophthalmitis, preseptal and orbital cellulitis, darcryocystitis), kidney and urinary tract (e.g., epididymitis, intrarenal and perinephric absces, toxic shock syndrome), skin (e.g., impetigo, folliculitis, cutaneous abscesses, cellulitis, wound infection, bacterial myositis) bone and joint (e.g., septic arthritis, osteomyelitis).

Preferably the antibody is prepared by expression of a DNA polymer encoding said antibody in an appropriate expression system such as described above for the expression of polypeptides of the invention. The choice of vector for the expression system will be determined in part by the host, which may be a prokaryotic cell, such as *E. coli* (preferably strain B) or Streptomyces sp. or a eukaryotic cell, such as a mouse C127, mouse myeloma, human HeLa, Chinese hamster ovary, filamentous or unicellular fungi or insect cell. The host may also be a transgenic animal or a transgenic plant (for example, as described in Hiatt, A. et al., *Nature* 340:76–78(1989). Suitable vectors include plasmids, bacteriophages, cosmids and recombinant viruses, derived from, for example, baculoviruses and vaccinia.

Polypeptide variants include antigenically, epitopically or immunologically equivalent variants that form a particular aspect of this invention. The term "antigenically equivalent derivative" as used herein encompasses a polypeptide or its equivalent which will be specifically recognized by certain antibodies which, when raised to the protein or polypeptide according to the invention, interfere with the immediate physical interaction between pathogen and mammalian host. The term "immunologically equivalent derivative" as used herein encompasses a peptide or its equivalent which when used in a suitable formulation to raise antibodies in a vertebrate, the antibodies act to interfere with the immediate physical interaction between pathogen and mammalian host.

The polypeptide, such as an antigenically or immunologically equivalent derivative or a fusion protein thereof is used as an antigen to immunize a mouse or other animal such as a rat or chicken. The fusion protein may provide stability to the polypeptide. The antigen may be associated, for example by conjugation, with an immunogenic carrier protein for example bovine serum albumin (BSA) or keyhole limpet haemocyanin (KLH). Alternatively a multiple antigenic peptide comprising multiple copies of the protein or polypeptide, or an antigenically or immunologically equivalent polypeptide thereof may be sufficiently antigenic to improve immunogenicity so as to obviate the use of a carrier.

Preferably, the antibody or variant thereof is modified to make it less immunogenic in the individual. For example, if the individual is human the antibody may most preferably be "humanized" ; where the complimentarity determining region(s) of the hybridoma-derived antibody has been transplanted into a human monoclonal antibody, for example as described in Jones, P. et al. (1986), *Nature* 321, 522–525 or Tempest et al., (1991) *Biotechnology* 9, 266–273. The humanized monoclonal antibody, or its fragment having binding activity, form a particular aspect of this invention.

The modification need not be restricted to one of "humanization" ; other primate sequences (for example Newman, R. et al., *Biotechnology* 10:1455–1460 (1992)) may also be used.

The use of a polynucleotide of the invention in genetic immunization will preferably employ a suitable delivery method such as direct injection of plasmid DNA into muscles (Wolff et al., Hum Mol Genet 1992, 1:363, Manthorpe et al., Hum. Gene Ther. 1963:4, 419), delivery of DNA complexed with specific protein carriers (Wu et al., *J Biol Chem.* 1989: 264,16985), coprecipitation of DNA with calcium phosphate (Benvenisty & Reshef, *PNAS USA,* 1986:83,9551), encapsulation of DNA in various forms of liposomes (Kaneda et al., *Science* 1989:243,375), particle bombardment (Tang et al., *Nature* 1992, 356:152, Eisenbraun et al., *DNA Cell Biol* 1993, 12:791) and in vivo infection using cloned retroviral vectors (Seeger et al., *PNAS USA* 1984:81,5849).

Vaccines

Another aspect of the invention relates to a method for inducing an immunological response in an individual, particularly a mammal which comprises inoculating the individual with SRP, or a fragment or variant thereof, adequate to produce antibody and/ or T cell immune response to protect said individual from infection, particularly bacterial infection and most particularly *Staphylococcus aureus* infection. Also provided are methods whereby such immunological response slows bacterial replication. Yet another aspect of the invention relates to a method of inducing immunological response in an individual which comprises delivering to such individual a nucleic acid vector to direct expression of SRP, or a fragment or a variant thereof, for expressing SRP, or a fragment or a variant thereof in vivo in order to induce an immunological response, such as, to produce antibody and/ or T cell immune response, including, for example, cytokine-producing T cells or cytotoxic T cells, to protect said individual from disease, whether that disease is already established within the individual or not. One way of administering the gene is by accelerating it into the desired cells as a coating on particles or otherwise. Such nucleic acid vector may comprise DNA, RNA, a modified nucleic acid, or a DNA/RNA hybrid.

A further aspect of the invention relates to an immunological composition which, when introduced into an individual capable or having induced within it an immunological esponse, induces an immunological response in such individual to a SRP or protein coded herefrom, wherein the composition comprises a recombinant SRP or protein coded therefrom comprising DNA which codes for and expresses an antigen of said SRP or protein coded therefrom. The immunological response may be used therapeutically or prophylactically and may take the form of antibody immunity or cellular immunity such as that arising from CTL or CD4+T cells.

A Ffh polypeptide or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as lipoprotein D from *Hemophilus influenzae*, Glutathione-S-transferase (GST) or beta-galactosidase, relatively large co-proteins which solubilize the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the polypeptides or polynucleotides of the invention and immunostimulatory DNA sequences, such as those described in Sato, Y. et al. Science 273: 352 (1996).

Also, provided by this invention are methods using the described polynucleotide or particular fragments thereof which have been shown to encode non-variable regions of bacterial cell surface proteins in DNA constructs used in such genetic immunization experiments in animal models of infection with *Staphylococcus aureus* will be particularly useful for identifying protein epitopes able to provoke a prophylactic or therapeutic immune response. It is believed that this approach will allow for the subsequent preparation of monoclonal antibodies of particular value from the requisite organ of the animal successfully resisting or clearing infection for the development of prophylactic agents or therapeutic treatments of bacterial infection, particularly *Staphylococcus aureus* infection, in mammals, particularly humans.

The polypeptide may be used as an antigen for vaccination of a host to produce specific antibodies which protect against invasion of bacteria, for example by blocking adherence of bacteria to damaged tissue. Examples of tissue damage include wounds in skin or connective tissue caused, e.g., by mechanical, chemical or thermal damage or by implantation of indwelling devices, or wounds in the mucous membranes, such as the mouth, mammary glands, urethra or vagina.

The invention also includes a vaccine formulation which comprises an immunogenic recombinant protein of the invention together with a suitable carrier. Since the protein may be broken down in the stomach, it is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation insotonic with the bodily fluid, preferably the blood, of the individual; and aqueous and non-aqueous sterile suspensions which may include suspending agents or thickening agents. The formulations may be presented in unit-dose or multi-dose containers, for example, sealed ampules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain Ffh protein, it is to be understood that this covers fragments of the naturally occurring protein and similar proteins with additions, deletions or substitutions which do not substantially affect the immunogenic properties of the recombinant protein.

Compositions, Kits and Administration

The invention also relates to compositions comprising the polynucleotide or the polypeptides discussed above or their agonists or antagonists. The polypeptides of the invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters.

The composition of the invention may be administered by injection to achieve a systemic effect against relevant bacteria shortly before insertion of an in-dwelling device. Treatment may be continued after surgery during the in-body time of the device. In addition, the composition could also be used to broaden perloperative cover for any surgical technique to prevent bacterial wound infections, especially Staphylococcus aureus wound infections.

Many orthopaedic surgeons consider that humans with prosthetic joints should be considered for antibiotic prophylaxis before dental treatment that could produce a bacteremia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1 µg/ml to 10 mg/ml for bathing of wounds or indwelling devices.

A vaccine composition is conveniently in injectable form. Conventional adjuvants may be employed to enhance the immune response. A suitable unit dose for vaccination is 0.5–5 microgram/kg of antigen, and such dose is preferably administered 1–3 times and with an interval of 1–3 weeks. With the indicated dose range, no adverse toxicological effects will be observed with the compounds of the invention which would preclude their administration to suitable individuals.

Each reference disclosed herein is incorporated by reference herein in its entirety. Any patent application to which this application claims priority is also incorporated by reference herein in its entirety.

EXAMPLES

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

All examples were carried out using standard techniques, which are well known and routine to those of skill in the art, except where otherwise described in detail. Routine molecular biology techniques of the following examples can be carried out as described in standard laboratory manuals, such as Sambrook et al., MOLECULAR CLONING: A LABORATORY MANUAL, 2nd Ed.; Cold Spring Harbor Laboratory Press, Cold Spring Harbor, N.Y. (1989).

All parts or amounts set out in the following examples are by weight, unless otherwise specified.

Unless otherwise stated size separation of fragments in the examples below was carried out using standard techniques of agarose and polyacrylamide gel electrophoresis ("PAGE") in Sambrook et al., MOLECULAR CLONING: A LABORATORY MANUAL, 2nd Ed., Cold Spring Harbor Laboratory Press, Cold Spring Harbor, N.Y. (1989) and numerous other references such as, for instance, by Goeddel et al., Nucleic Acids Res. 8: 4057 (1980).

Example 1

Strain Selection, Library Production and Sequencing

The polynucleotide having the DNA sequence given in SEQ ID NO:1 was obtained from a library of clones of chromosomal DNA of Staphylococcus aureus in E. coli. The sequencing data from two or more clones containing overlapping Staphylococcus aureus DNAs was used to construct the contiguous DNA sequence in SEQ ID NO:1. Libraries may be prepared by routine methods, for example: Methods 1 and 2 below.

Total cellular DNA is isolated from Staphylococcus aureus WCUH 29 according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and E.coli infected with the packaged library. The library is amplified by standard procedures.

Method 2

Total cellular DNA is partially hydrolyzed with a one or a combination of restriction enzymes appropriate to generate a series of fragments for cloning into library vectors (e.g., RsaI, PalI, AluI, Bshl235I), and such fragments are size-fractionated according to standard procedures. EcoRI linkers are ligated to the DNA and the fragments then ligated into the vector Lambda ZapII that have been cut with EcoRI, the library packaged by standard procedures, and E.coli infected with the packaged library. The library

What is claimed is:

1. An isolated polynucleotide segment comprising: a first polynucleotide sequence, or the full complement of the entire length of the first polynucleotide sequence, wherein the first polynucleotide sequence is selected from the group consisting of:

(a) a polynucleotide comprising a polynucleotide as set forth in SEQ ID NO:1; and, (b) a nucleic acid sequence identical to the polynucleotide of (a) except that, over the entire length corresponding to the polynucleotide of (a), up to thirty nucleotides are substituted, deleted or inserted for every 100 nucleotides of the polynucleotide of (a)

and wherein the first polvnucleotide sequence detects *Staphylococcus aureus*.

2. A vector comprising the isolated polynucleotide segment of claim 1.

3. An isolated host cell comprising the vector of claim 2.

4. The isolated polynucleotide segment of claim 1, wherein the first polynucleotide sequence is a nucleic acid sequence identical to the polynucleotide of (a) except that, over the entire length corresponding to the polynucleotide of (a), up to ten nucleotides are substituted, deleted or inserted for every 100 nucleotides of the polynucleotide of (a).

5. The isolated polynucleotide segment of claim 1, wherein the first polynucleotide sequence is a nucleic acid sequence identical to the polynucleotide of (a) except that, over the entire length corresponding to the polynucleotide of (a), up to five nucleotides are substituted, deleted or inserted for every 100 nucleotides of the polynucleotide of (a).

6. The isolated polynucleotide segment of claim 1, wherein the first polynucleotide sequence is the polynucleotide of (a).

7. An isolated polynucleotide segment, comprising a first polynucleotide sequence or the full complement of the entire length of the first polynucleotide sequence, wherein the first polynucleotide sequence hybridizes to the full complement of SEQ ID NO:1, wherein the hybridization conditions include incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml denatured, sheared salmon sperm DNA, followed by washing in 0.1×SSC at 65° C.; and wherein the first polynucleotide sequence is identical to nucleotides 1 to 1365 of SEQ ID NO:1 except that, over the entire length corresponding to SEQ ID NO:1, up to five nucleotides are substituted, deleted or inserted for every 100 nucleotides of SEQ ID NO:1; and wherein the first polynucleotide sequence detects *Staphylococcus aureus*.

8. The isolated polynucleotide segment of claim 7, wherein the hybridization conditions include incubation at 42° C. in a solution comprising: 50% formamide, 5×SSC (150 mM NaCl, 15 mM trisodium citrate), 50 mM sodium phosphate (pH7.6), 5×Denhardt's solution, 10% dextran sulfate, and 20 micrograms/ml denatured, sheared salmon sperm DNA, followed by washing in 0.1×SSC at 65° C.; and, wherein the first polynucleotide sequence is identical to nucleotides 1 to 1365 of SEQ ID NO:1 except that, over the entire length corresponding to SEQ ID NO:1, up to three nucleotides are substituted, deleted or inserted for every 100 nucleotides of SEQ ID NO:1.

9. An isolated polynucleotide segment comprising a first polynucleotide sequence, or the full complement of the entire length of the first polynucleotide sequence, wherein the first polynucleotide sequence is a polynucleotide encoding a polypeptide consisting of SEQ ID NO:4.

10. The isolated polynucleotide segment of claim 9, wherein the first polynucleotide sequence comprises SEQ ID NO:3.

* * * * *